United States Patent [19]

Khan et al.

[11] Patent Number: 4,904,480

[45] Date of Patent: Feb. 27, 1990

[54] RADIATION COMPATIBLE IODINE FORMULATION

[75] Inventors: Mohammed A. Khan, Sandy; John F. Moellmer, Salt Lake City, both of Utah

[73] Assignee: Becton, Dickinson and Company, Franklin Lakes, N.J.

[21] Appl. No.: 245,484

[22] Filed: Sep. 19, 1988

[51] Int. Cl.$^4$ .............................................. A61K 33/36
[52] U.S. Cl. .................................................... 424/667
[58] Field of Search ................................. 424/150, 667

[56] References Cited

U.S. PATENT DOCUMENTS

| | | | |
|---|---|---|---|
| 4,113,857 | 9/1978 | Shetty | 424/150 |
| 4,576,818 | 3/1986 | Shetty | 424/150 |
| 4,668,510 | 5/1987 | Shetty | 424/150 |

Primary Examiner—Allen J. Robinson
Assistant Examiner—Zohreh A. Fay
Attorney, Agent, or Firm—Richard E. Brown

[57] ABSTRACT

A germicidal iodine-containing composition includes iodine, an iodophor, cupric ions and nitrite ions in an aqueous base. Iodide ions which form in the composition during radiation sterilization or prolonged shelf life are oxidized back to iodine by the cupric ions in a pH dependent reaction which consumes hydrogen ions formed concurrently with the iodide ions. Cuprous ions formed during the oxidation are spontaneously cycled back to cupric ions by traces of air present in the composition. The composition may include nitrite ions to augment the conversion of cuprous ions back to the cupric form.

14 Claims, No Drawings

RADIATION COMPATIBLE IODINE FORMULATION

BACKGROUND OF THE INVENTION

1. Field of the Invention

This invention relates to germicidal compositions, and more particularly relates to iodine compositions which are not degraded during radiation sterilization or prolonged shelf life.

2. Background

Iodine is a well-known germicide with activity against a wide range of bacteria and viruses, and much effort has been directed to finding satisfactory vehicles for its administration. Carriers of iodine which are often used are termed iodophors. Iodophors are generally polymeric materials, such as surfactants and polyvinylpyrrolidone (povidone) which form complexes with iodine.

In some cases, an iodophor-iodine complex is impregnated into a sponge or brush used for germicidal cleansing or scrubbing. Often, such implements are included in a kit of materials which may also include other items useful for patient preparation, such as towels, gloves and the like. Such kits must be sterilized at some time prior to their use, usually at the time of manufacture. Gamma radiation is an effective sterilizing process, however, irradiation is known to decrease significantly the quantity of available iodine by conversion to iodide ion with consequent reduction in antibacterial activity.

Other problems arise in the use of iodine as a germicide. A typical iodine product, whether sterilized or not, continuously loses iodine during its shelf life. Iodophors are generally used in an aqueous base, and, in the presence of water, iodine undergoes a well-known but complex series of reactions leading, among other species, to iodide ions and hydrogen ions. The production of hydrogen ions may reduce the pH of a topical iodine preparation enough to cause skin irritation and discomfort to the user. Loss of iodine titer causes an additional problem of assuring that the iodine content of a composition does not fall below the stated concentration on the label during its time on the shelf.

Accordingly, a variety of approaches has focused on ways to stabilize the iodine concentration in an iodophor-iodine complex. U.S. Pat. No. 4,271,149 to Winicov et al. discloses a germicidal iodine composition of stabilized iodine concentration. The composition contains an organic material, iodine, iodide ion and iodate ion and is maintained at a pH of from 5 to 7 wherein the iodide and iodate react in the presence of hydrogen ions to replenish iodine lost during storage.

U.S. Pat. No. 4,113,857 to Shetty discloses a method to stabilize a preformed iodophor-iodine complex by adding an oxidizing agent, such as iodate ion, and to prepare a complex by reacting an iodophor, such as povidone, with iodate and iodide ions.

An iodine-surfactant germicidal cleansing composition is disclosed in U.S. Pat. No. 4,597,975 to Woodward et al. In the Woodward et al. composition, low concentrations of iodine are stabilized as the triiodide salt by complexing with an amine oxide surfactant. When solubilized by excess amine oxide, the triiodide salt has a very low iodine vapor pressure and high germicidal activity.

Bunting et al., in U.S. Pat. No. 4,427,631, discloses a method to radiation-sterilize a povidone-iodine composition. Iodide ion and iodate ion are added to the composition prior to irradiation to prevent radiation-induced gelation of the povidone and radiation-induced decrease in the amount of available iodine.

Although the above disclosures have improved iodophor stability during sterilization and shelf time, there remains a need for further improvement, particularly during a prolonged shelf life. It is toward fulfillment of this need that the present invention is directed.

SUMMARY OF THE INVENTION

A germicidal composition includes iodine, an iodophor and cupric ions in an aqueous solution. The preferred iodophor is povidone. Most preferably, the iodine and iodophor may be a quantity of povidone iodine (hereinafter PVP-I) wherein the iodine concentration in the composition may be from about 0.09 to 2.4% by weight (all percentages in the present disclosure are given in weight percent). Other iodophors such as conventional surfactants, preferably nonionic surfactants, may be used in place of or in conjunction with povidone. In the most preferred composition, the PVP-I is the United States Pharmacopeia defined material, hereinafter PVP-I (USP).

Iodide ions and hydrogen ions present in the composition as a result of decomposition of the iodine, whether caused by radiation sterilization, degradation caused by passage of time or any other reason, are removed by a cyclic reaction system in which iodide ions are oxidized to iodine by the cupric ions thereby maintaining a substantially stable iodine concentration. Cuprous ions formed by reduction of cupric ions are spontaneously reoxidized back to cupric ions by traces of air in the composition in a pH dependent reaction which consumes the hydrogen ions, thereby providing pH control.

Since the reoxidation of cuprous ions to cupric ions is pH dependent and proceeds more rapidly at low pH, it slows down as the hydrogen ions are consumed. Accordingly, the preferred composition includes an oxidizing agent to provide more rapid regeneration of cupric ions. The preferred oxidizing agent is an alkali metal nitrite.

The composition may contain other ingredients conventional in germicidal and cosmetic compositions, such as buffers, thickeners, emollients, foam stabilizers, perfumes, dyes and the like.

Thus, the invention provides a germicidal iodine-containing composition wherein cupric ion reacts with iodide ion to initiate a cyclic system which converts iodide and hydrogen ions to iodine and water respectively without consumption of the cupric ion. Control of both pH and iodine concentration are achieved with a catalytic quantity of cupric ion.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The present invention is directed to a germicidal iodine composition in which the iodine concentration and pH remain stable during radiation sterilization and subsequent extended shelf life. Although the iodine composition of the invention may be formulated with any suitable iodophor, the invention will be described in terms of the preferred iodophor, povidone.

PVP-I is the active ingredient in a variety of commercial germicidal preparations, for example PVP-I topical aerosol solution, PVP-I ointment, PVP-I cleansing solution and PVP-I topical solution. PVP-I (USP) contains not less than 9.0% and not more than 12.0% of available iodine. This material contains some iodide ion, specified to be 6.6% or less.

The composition of the present invention may contain from about 0.09 to 2.4% iodine. This quantity of iodine is preferably introduced into the composition as about 1 to 20% PVP-I (USP). Preferably, about 6 to 12%, most preferably about 7 to 10% of PVP-I (USP) may be used. In the composition of the invention, the PVP-I may be dissolved in any suitable solvent. Alcohols such as ethanol may be used, or the alcohol may be mixed in any proportion with water. Preferably, a calculated quantity of water purified by a procedure such as deionization may be used.

As will be described later, the composition of the invention includes cupric ion as part of a cycling system which consumes hydrogen ions and prevents any substantial reduction in the pH during radiation sterilization and prolonged shelf life. Control of the pH may, if desired, be augmented by addition of a buffer to maintain the pH of the composition from about 5 to 7, preferably about 5 to 6, most preferably about 5. Suitable buffers are sodium bicarbonate, ammonium acetate, dibasic sodium phosphate, and, most preferably, sodium citrate.

A cupric salt may be added to the aqueous solution of PVP-I. Although any soluble cupric salt, such as the chloride may be used, the preferred salt is the sulfate. The concentration of the cupric salt is not critical. Since the cupric ion is readily regenerated from the cuprous state on standing in solution, a very low concentration of cupric ion, which may be from about 0.001 to 0.1% based on the copper, preferably about 0.01 to 0.05%, may be used.

In accordance with the invention, the cupric ion oxidizes iodide ion to iodine according to equation 1.

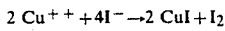  1

Thus, iodide ion present in PVP-I, iodide ion generated during radiation sterilization, and iodide ion resulting from reaction of iodine and water over time will be converted to iodine according to equation 1.

It is well-known that most cuprous salts tend to undergo facile oxidation to the cupric state. Applicants have found that the cuprous iodide formed in equation 1 is oxidized back to the cupric state by traces of air or other oxidizing agents in the composition. This reaction is illustrated by equation 2.

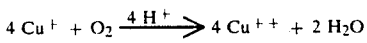  2

It is readily seen that equations 1 and 2 together constitute a cycling system in which the cupric ion is not consumed during conversion of the iodide to iodine, as illustrated in equation 3.

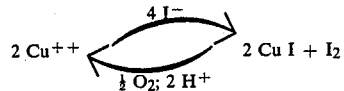  3

Although the cupric ion is present in the composition of the invention in very small quantities and there is no net consumption of cupric ion, it is not a true catalyst because it does enter the reaction.

The reaction of equation 2 is seen to be pH dependent, and is very rapid at low pH. At the preferred weakly acidic pH of the composition of the invention, determined as described above by the choice of buffer, the cyclic reactions of equation 3 are less rapid. Although slower, the reactions of equation 3 are sufficient to maintain a stable iodine concentration during shelf time. For rapid stabilization, the preferred composition of the invention includes an oxidizing agent to enhance the reactions of cycling system 3.

Any conventional water soluble oxidizing agent may be included in the composition of the invention to accelerate conversion of the cuprous iodide back to cupric ion. Exemplary of suitable oxidizing agents are iodate, chlorate, nitrite, nitrate and sulfite. The preferred oxidizing agent is nitrite ion, preferably added to the composition as an alkali metal nitrite. Nitrite ion oxidizes cuprous iodide according to the reaction of equation 4.

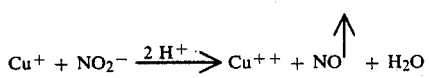  4

A suitable range of nitrite ion concentration is from about 0.003% to 0.1%.

Iodophors other than povidone may serve as the iodine carrier in the composition of the invention, or a mixture of povidone and another iodophor may be used. The iodophor may be any conventional surfactant of the cationic, anionic, amphoteric, or, preferably nonionic classes. Exemplary of, but not limited to, such surfactants are Igepal® alkylphenoxypoly(ethyleneoxy) alcohols available from GAF Chemicals Corp., Wayne, N.J., the Pluronic® polyalkyleneoxyglycols available from BASF Wyandotte Corp., Parsippany, N.J., the Barlox® amine oxides available from Lonza, Inc. Fair Lawn, N.J. and the Neodol® ethoxylated primary alcohols available from Shell Chemical Co., Houston, Tex. The quantity of surfactant to be added is not critical, and may be anywhere from about 1 to 25%. A preferred range of surfactant concentration is 1 to 10%. Most preferably, about 1.8 to 4.0% of surfactant is included in the composition of the invention.

Other ingredients conventionally added to pharmaceutical formulations may be included. For example, thickening agents, foam stabilizers such as Gafamide (Cocodiethanolamide, GAF Corp., Wayne, N.J.) and emollients may be added. Suitable emolients are, for example, mineral oil, Arlamol-E polyoxypropylene 15 stearyl ether (ICI Americas, Wilmington, Del.), Solulan—polyethylene qlycol lanolin (Amerchol, Edison, N.J.) or Acetulan—cetyl acetate (and) acetylated lanolin alcohol (Amerchol, Edison, N.J.). A fragrance compound and dye may be added to qive the composition a pleasing scent and color. A variety of suitable fragrance compounds, selected as to preference, is available from International Flavers and Fraqrances, Inc., Union Beach, N.J. Likewise, a variety of dyes, also selected as to preference, is available from Tricon Colors, Inc., Elmwood Park, N.J.

The composition of the invention may be incorporated into a surgical scrub package containing conventional components such as, for example, a sponge, brush and nail pick. Preferably, a foam sponge and a polyethylene brush are combined into a single assembly.

The composition and the package have been analyzed for changes in available iodine, in accordance with Examples I–III and changes in pH resulting from sterilization by exposure to 2.5 Mrad of radiation. Representative compositions are delineated in Chart I, and available iodine and pH before and after radiation sterilization are given in Charts II and III respectively.

CHART I

| Ingredients | COMPOSITION[a] | | | | | | | | |
|---|---|---|---|---|---|---|---|---|---|
| | 1 | 2 | 3 | 4 | 5 | 6 | 7 | 8 | 9 |
| Water, purified | 79.0 | 84.25 | 83.0 | 78.85 | 84.137 | 82.85 | 78.925 | 83.0 | 82.85 |
| Pluronic L-35[b] | 3.0 | 2.25 | 1.8 | 3.00 | 2.250 | 1.80 | 3.000 | 3.0 | 3.00 |
| Neodol 25-3A[c] | 3.0 | 2.25 | 1.8 | 3.00 | 2.250 | 1.80 | 3.000 | 3.0 | 3.00 |
| Barlox 12[d] | 4.0 | 3.00 | 2.4 | 4.00 | 3.000 | 2.40 | 4.000 | — | — |
| Sodium Citrate | 1.0 | 0.75 | 1.0 | 1.00 | 0.750 | 1.00 | 1.000 | 1.0 | 1.00 |
| PVP-I | 10.0 | 7.50 | 10.0 | 10.00 | 7.500 | 10.00 | 10.000 | 10.0 | 10.00 |
| $CuSO_4 \cdot 5H_2O$ | — | — | — | 0.05 | 0.038 | 0.05 | 0.025 | — | 0.05 |
| Sodium Nitrate | — | — | — | 0.10 | 0.075 | 0.10 | 0.050 | — | 0.10 |

[a] % by weight
[b] poly(oxypropylene)poly(oxyethylene) condensate
[c] ethoxylate of $C_{12}$-$C_{15}$ alcohols containing 3 oxyethylene groups
[d] cocamine oxide

CHART II

| | AVAILABLE IODINE[a] | | | | | |
|---|---|---|---|---|---|---|
| COM-POSI-TION | BULK | | | PACKAGED | | |
| | Initial | Irr.[b] | % change | Initial | Irr.[b] | % change |
| 1 | 1.03 | 0.76 | 23.3 | 0.70 | 0.43 | 38.6 |
| 2 | 0.73 | 0.50 | 31.5 | 0.41 | 0.30 | 26.8 |
| 3 | 1.03 | 0.79 | 26.2 | 0.70 | 0.48 | 31.4 |
| 4 | 1.17 | 1.00 | 14.5 | 0.78 | 0.70 | 10.3 |
| 5 | 0.80 | 0.72 | 10.0 | 0.51 | 0.41 | 19.6 |
| 6 | 1.12 | 0.99 | 11.6 | 0.81 | 0.66 | 18.5 |
| 7 | 1.07 | 0.94 | 12.1 | 0.77 | 0.55 | 28.6 |
| 8 | 1.06 | 0.83 | 21.7 | 0.87 | 0.59 | 32.2 |
| 9 | 1.14 | 1.04 | 8.8 | 0.95 | 0.87 | 8.1 |

[a] determined according to Example III
[b] irradiated

CHART III

| | MEASURED pH[a] | | | | | |
|---|---|---|---|---|---|---|
| COM-POSI-TION | BULK | | | PACKAGED | | |
| | Initial | Irr | % change | Initial | Irr | % change |
| 1 | 4.56 | 4.05 | 11.2 | 4.55 | 4.17 | 8.4 |
| 2 | 4.55 | 3.85 | 15.4 | 4.53 | 4.27 | 5.7 |
| 3 | 4.60 | 4.05 | 12.0 | 4.55 | 4.31 | 5.3 |
| 4 | 4.7 | 4.6 | 2.1 | 4.90 | 4.82 | 1.6 |
| 5 | 4.8 | 4.7 | 2.1 | 4.99 | 4.88 | 2.2 |
| 6 | 4.8 | 4.7 | 2.1 | 4.97 | 4.90 | 1.4 |
| 7 | 4.75 | 4.50 | 5.3 | 4.83 | 4.65 | 3.7 |
| 8 | 4.65 | 4.15 | 10.7 | 4.77 | 4.10 | 14.0 |
| 9 | 4.6 | 4.5 | 2.1 | 4.96 | 4.65 | 6.2 |

[a] determined with a Corning Model M120 pH meter, Corning Scientific Instruments, Madfield, Massachusetts It is seen from Chart I that the compositions (1, 2, 3 and 8) lacking cupric ion and nitrite ion have an average decrease in available iodine of 25.7% in bulk material and 32.1% in packaged material due to the radiation. This may be compared with compositions 4–7 and 9 of the invention including both ions which show an average decrease in available iodine of 11.4% in bulk material and 17.0% in packaged material.

Likewise, Chart III shows that the compositions lacking cupric and nitrite ions have an average decrease in pH of 12.3% in bulk material and 8.4% in packaged material due to the radiation. In contrast, compositions 4–7 and 9 of the invention show an average decrease in pH of 2.7% in bulk material and 3.0% in packaged material due to the radiation.

The following examples are provided to further illustrate the invention, but the specific details therein are not to be considered as limitative of the invention.

EXAMPLE I

Preferred Composition of the Invention

| Preferred Composition of the Invention | |
|---|---|
| PVP-I | 10.00% |
| Pluronic ® L-35 | 3.00% |
| Neodol ® 25-3A | 3.00% |
| Sodium Citrate | 1.00% |
| Copper Sulfate - 5 hyd. | 0.05% |
| Sodium Nitrite | 0.10% |
| Water, purified | 83.85% |

EXAMPLE II

Preparation of the Composition of Example I and Incorporation Thereof Into A Package In a suitably sized vessel equipped for mixing was placed 82.85 g of purified water, 10.00 g of PVP-I, and 3.00 g of Pluronic ® L-35. After thorough mixing, Neodol ® 25-3A, 3.00 g, was added with mixing. Sodium citrate, 1.00 g, was added and mixed well. Copper sulfate pentahydrate, 0.05 g, was added and mixed well. Sodium nitrite, 0.10 g, was added and the mixture was thoroughly mixed to ensure complete homogeneity. The mixture was adjusted, if necessary, to pH 6.0 by the addition of either 6N HCl or 50% NaOH. Thirty-three ml of this solution was then automatically injected into a foam sponge/polyethylene brush assembly which together with a nail pick is packaged into a single disposable surgical scrub unit.

EXAMPLE III

Method of Analysis of Available Iodine in Packaged Surgical Scrub Units

The scrub unit of Example II was weighed, opened and the contents (brush/sponge assembly and iodophor solution) transferred quantitatively into a 1000 ml beaker by rinsing the package with distilled water. Sufficient water to completely immerse the brush/sponge assembly, but not to exceed approximately 300 ml of the total solution, was added. The contents of the beaker were surged with a surging instrument and then titrated with sodium thiosulfate until the solution became just clear. The solution was surged again, allowed to stand for 10 minutes, and titrated again with sodium thiosulfate to the end point. The total volume of sodium thiosulfate used in the titration was determined, and the brush/sponge assembly was carefully removed from the beaker and rinsed in tap water. All contents of the package along with the package were dried in the oven and weighed. The difference between the initial weight and this final weight was the weight of the iodophor solution. Available iodine was calculated according to the following equation:

$$\text{Available Iodine (\%)} = \frac{\text{(Vol. of Sod. Thiosulfate)(Normality of Sod. Thiosulfate)}(12.69)}{\text{Weight of Iodophor Solution}}$$

Thus, the invention provides an iodophor composition including cupric ion which acts to control both iodine concentration and pH by a cycling mechanism. Because of the cycling feature whereby continual regeneration of cupric ion takes place, only very small quantities of the control additive are needed. An iodine composition which is particularly suitable for topical administration is achieved as a result of the stable iodine concentration and pH.

What is claimed is:

1. A germicidal iodophor composition comprising an aqueous solution of about 1 to 20% by weight of povidone iodine having about 9–12% by weight iodine therein, about 0.001 to 0.1% by weight of a soluble cupric salt and about 0.001 to 0.1% by weight of a water soluble oxidizing agent, said cupric salt being capable of oxidizing iodide ions in said composition to iodine, said oxidizing agent being capable of oxidizing cuprous ions to cupric ions, whereby the pH and the iodine concentration in said composition remain substantially unchanged.

2. The composition of claim 1 wherein said povidone iodine is USP povidone iodine.

3. The composition of claim 1 wherein said salt is cupric sulfate.

4. The composition of claim 1 wherein said oxidizing agent is selected from the group consisting of an alkali metal nitrite, sulfite, nitrate and chlorate.

5. The composition of claim 1 further comprising an ingredient selected from the group consisting of a surfactant, thickening agent, an emollient, a foam stabilizer, a fragrance compound and a dye.

6. The composition of claim 5 wherein said surfactant is a nonionic surfactant.

7. The composition of claim 6 wherein said nonionic surfactant is selected from the group consisting of an alkylphenoxypoly(ethyleneoxy) alcohol, a polyalkyleneoxyglycol, an amine oxide and an ethoxylated primary alcohol.

8. A germicidal iodophor composition comprising:
an aqueous solution of about 6 to 12% by weight of povidone iodine, about 1 to 10% by weight of a nonionic surfactant, a buffer adapted to maintain the pH of said solution from 5 to 6.5, about 0.01 to 0.1% by weight of a soluble cupric salt and about 0.01 to 0.1% by weight of a nitrite salt, said cupric salt being capable of oxidizing iodide ions in said composition to iodine, said nitrite salt being capable of oxidizing cuprous ions to cupric ions, whereby the pH and the iodine concentration in said composition remain substantially unchanged.

9. The composition of claim 8 wherein said salt is cupric sulfate.

10. The composition of claim 8 wherein said nitrite salt is an alkali metal nitrite.

11. A surgical scrub package comprising a sponge and brush, said sponge and brush having incorporated therein a germicidally effective quantity of the composition of claim 8.

12. The package of claim 11 wherein said sponge is of foam.

13. The package of claim 11 wherein said brush is of polyethylene.

14. The package of claim 11 wherein said sponge and brush are combined in an assembly.

* * * * *